United States Patent
Zheng et al.

(10) Patent No.: US 9,743,892 B2
(45) Date of Patent: Aug. 29, 2017

(54) IMAGE DISTORTION CORRECTION AND ROBUST PHANTOM DETECTION

(71) Applicant: UNIVERSITAT BERN, Bern (CH)

(72) Inventors: Guoyan Zheng, Bern (CH); Steffen Schumann, Bern (CH)

(73) Assignee: UNIVERSITAT BERN, Bern (CH)

( * ) Notice: Subject to any disclaimer, the term of this patent is extended or adjusted under 35 U.S.C. 154(b) by 205 days.

(21) Appl. No.: 14/398,130

(22) PCT Filed: Apr. 30, 2013

(86) PCT No.: PCT/EP2013/059057
§ 371 (c)(1),
(2) Date: Oct. 31, 2014

(87) PCT Pub. No.: WO2013/164368
PCT Pub. Date: Nov. 7, 2013

(65) Prior Publication Data
US 2015/0085979 A1    Mar. 26, 2015

(30) Foreign Application Priority Data

May 1, 2012 (EP) .................................. 12166279

(51) Int. Cl.
A61B 6/04      (2006.01)
G06K 9/20      (2006.01)
(Continued)

(52) U.S. Cl.
CPC ............ *A61B 6/0492* (2013.01); *A61B 6/582* (2013.01); *A61B 6/583* (2013.01); *A61B 6/584* (2013.01);
(Continued)

(58) Field of Classification Search
CPC ........... A61B 6/00; A61B 6/04; A61B 6/0492; A61B 6/54; A61B 6/58;
(Continued)

(56) References Cited

U.S. PATENT DOCUMENTS 6,049,582 A * 4/2000 Navab .................. A61B 6/4441
378/17
6,206,566 B1 * 3/2001 Schuetz ................. A61B 6/547
378/205
(Continued)

FOREIGN PATENT DOCUMENTS

EP        2543320        1/2013
WO    2012/150336 A1    11/2012

OTHER PUBLICATIONS

Li, Xinhua, et al "A Generic Geometric Calibration Method for Tomographic Imaging Systems with Flat Panel Detectors—A Detailed Implementation Guide", Jun. 29, 2010, Amer. Assoc. Phys. Med., Med. Phys., vol. 37, No. 7, pp. 3844-3854.*
(Continued)

*Primary Examiner* — Anastasia Midkiff
(74) *Attorney, Agent, or Firm* — JMB Davis Ben-David

(57) ABSTRACT

The invention relates to a method for detecting a phantom, comprising the steps of: arranging a phantom with respect to an object, acquiring at least one image of said object by means of an x-ray apparatus, such that the image contains projections of the object and projections of at least three first calibration fiducials of the phantom, detecting the projections of the at least three first calibration fiducials in said at least one image, and establishing a correspondence between the 2D image coordinates of said projections of the at least three first calibration fiducials and the 3D coordinates of said
(Continued)

at least three first calibration fiducials in a local coordinate system of the phantom for computing the projection matrix at least up to a scale factor.

17 Claims, 9 Drawing Sheets

(51) Int. Cl.
| | |
|---|---|
| *G06T 7/00* | (2017.01) |
| *G06K 9/78* | (2006.01) |
| *G06K 9/80* | (2006.01) |
| *A61B 6/00* | (2006.01) |
| *G06K 9/62* | (2006.01) |
| *G06T 5/00* | (2006.01) |
| *G06T 7/80* | (2017.01) |

(52) U.S. Cl.
CPC ......... *G06K 9/2063* (2013.01); *G06K 9/6203* (2013.01); *G06T 7/0014* (2013.01); *A61B 6/4441* (2013.01); *G06K 9/2054* (2013.01); *G06K 9/78* (2013.01); *G06K 9/80* (2013.01); *G06T 5/006* (2013.01); *G06T 7/80* (2017.01); *G06T 2207/10081* (2013.01); *G06T 2207/10116* (2013.01); *G06T 2207/20* (2013.01); *G06T 2207/30004* (2013.01); *G06T 2207/30204* (2013.01); *G06T 2211/40* (2013.01)

(58) Field of Classification Search
CPC ......... A61B 6/582–6/584; G02B 27/00; G02B 27/32; G02B 27/36; G01R 33/58; G06K 9/00; G06K 9/00013; G06K 9/20; G06K 9/2054; G06K 9/2063; G06K 9/36; G06K 9/60; G06K 9/62; G06K 9/6201–9/6203; G06K 9/6211; G06K 9/6232; G06K 9/6255; G06K 9/6261; G06K 9/6298; G06K 9/78; G06K 9/80; G06T 1/00; G06T 1/0007; G06T 5/00; G06T 5/006; G06T 2200/00; G06T 5/04; G06T 5/08; G06T 5/28; G06T 2207/00; G06T 2207/10; G06T 2207/10028; G06T 2207/10072; G06T 2207/10081; G06T 2207/20; G06T 2207/30; G06T 2207/30004; G06T 2211/00; G06T 2211/40; G06T 7/00; G06T 7/0012; G06T 7/0014; G06T 7/0022; G06T 7/0024; G06T 7/0026; G06T 7/0028; G06T 7/003; G06T 7/0032; G06T 7/0036; G06T 7/004; G06T 7/0042; G06T 7/0044; G06T 7/0046; G06T 7/0051; G06T 7/0065
See application file for complete search history.

(56) References Cited

U.S. PATENT DOCUMENTS

| | | | | |
|---|---|---|---|---|
| 6,379,041 | B1* | 4/2002 | Schuetz | A61B 6/583 378/205 |
| 6,826,423 | B1* | 11/2004 | Hardy | A61B 5/064 600/414 |
| 2004/0252811 | A1 | 12/2004 | Morita et al. | |
| 2009/0116621 | A1* | 5/2009 | Yuan | A61B 6/583 378/207 |
| 2011/0191084 | A1* | 8/2011 | Cooke | G06G 7/60 703/11 |
| 2013/0315440 | A1* | 11/2013 | Frank | G06K 9/3216 382/103 |

OTHER PUBLICATIONS

Mennessier, C., et al., "Distortion Correction, Geometric Calibration, and Volume Reconstruction for an Isocentric C-Arm X-ray System", 2011, IEEE Nuclear Science Symposium Conference Record, pp. 2943-2947.*
Yaniv, Z., et al.: Fluroscopic image processing for computer-aided orthopaedic surgery. MICCAI'98, LNCS 1496 (1998) 325-334.
Hofstetter, R. ,et al.: Fluoroscopy as an imaging means for computer assisted surgical navigation. Computer Aided Surgery 4(1999)65-76.
Livyatan, H., et al.: Robust automatic C-arm calibration for fluoroscopy-based navigation: a practical approach. MICCAI'02, LNCS 2489 (2002) 60-68.
Kainz, B., et al.: Fast marker based C-arm pose estimation. MICCAI'08, LNCS 5242 (2008) 652-659.
Chintalapani, G., Jain A.K., Taylor, R.H.: Statistical characterization of C-arm distortion with application to intra-operative distortion correction. SPIE Medical Imaging 2007, vol. 6509 (2007) 65092Y.1-65092Y.8.
Chintalapani, G., Taylor, R.H.: C-arm distortion correction using patient CT as fiducial. ISBI 2007, (2007) 1180-1183.
Yao, J., et al.: A C-arm fluoroscopy-guided progressive cut refinement strategy using a surgical robot. Computer Aided Surgery 5 (2000) 373-390.
Jain, A. and Fichtinger, G.: C-arm tracking and reconstruction without an external tracker. MICCAI'06, LNCS 4190 (2006)494-502.
Otake, Y., et al.: An iterative framework for improving the accuracy of intraoperative intensity-based 2D/3D registration for image-guided orthopedic surgery. IPCAI'I0, LNCS 6135 (2010)23-33.
Rajamani, K.T., et al.: Statistical deformable bone models for robust 3D surface extrapolation from sparse data. Medical Image Analysis, 11(2007)99-109.

* cited by examiner

IMAGE DISTORTION CORRECTION AND ROBUST PHANTOM DETECTION

FIELD

The invention relates to a method for detecting a phantom as well as to a method for image distortion correction that may be used in conjunction with the phantom detection. Particularly, the image distortion correction is based on a statistical model computed beforehand.

BACKGROUND

A fluoroscope, also known as a C-arm due to its "C" shape, is often used intra-operatively for visualizing underlying anatomy and surgical instruments. Though its applications in interventional disciplines are persuasive, its disadvantages are also apparent. A fluoroscopy image is a two-dimensional (2D) projection image, which lacks depth information. The image is distorted and has limited field of view. Its ability in providing three-dimensional (3D) quantitative information is limited and its application involves high radiation exposure to the interventional team. This has led to the development of methods for precise C-arm calibration[1,2,3,4], which are important for various fluoroscopy image based applications.

The goal of the calibration is to correct the geometric image distortion and to estimate the projection parameters of the x-ray apparatus (e.g. C-arm). For this purpose, a cage with fiducials arranged in multiple planes is normally required to be attached to the image intensifier, which has the disadvantage of interfering with the patient anatomy being imaged and requires tracking of the C-arm machine by an external tracker, which sometimes is judged to be too cumbersome.

There exist attempts to replace the external tracker with a mobile phantom. Yao et al.[7] proposed to use a line fiducial based phantom mounted on a robot's tool holder to register the end effector of the surgical robot to a C-arm image. Inspired by this work, Jain and Fichtinger[8] developed a new phantom that used ellipses and straight lines as fiducials in addition to points. Although encouraging results were presented with this new phantom[8], it was recently reported by Otake et al.[9] that automatic segmentation of this phantom from an intra-operatively acquired image was not always possible due to severe background clutter. They thus proposed to use a manually initialized, model-based iterative 2D-3D registration for an accurate detection of the phantom from the image.

Attempts to characterize the C-arm distortion with a statistical framework have previously been done by Chintalapani et al.[5,6]. Based on a statistical model of the geometrical image distortion, Chintalapani et al. discussed using fewer fiducials[5] or even using the patient CT[6] as a fiducial for distortion correction. The limitation of their work is that they only use images acquired from a fixed position by rotating the arm to build the statistical model of the distortion pattern such that the influence of the earth magnetic field on the image distortion was not estimated. It has been shown that such an influence contributes a lot to the image distortion and it is position dependent[2,7].

SUMMARY

Thus, the problem underlying the present invention is to provide for a method and a corresponding device that allows to correct for distortions in an image of an x-ray apparatus (for instance a fluoroscope such as a C-arm) due to the earth magnetic field and eventually other influences as well as to a method and a corresponding device for robust phantom detection that can be conducted in conjunction with the image distortion correction procedure, when necessary.

Concerning phantom detection, the problem underlying the present invention is solved by a method according to the present invention.

According thereto, the method for detecting a phantom, comprises the steps of: arranging a mobile phantom, i.e., a phantom that can be manually freely displaced, with respect to an object or a target anatomy (in this respect it is to be noted that, in a reference position, see below, the phantom is preferably rigidly attached to an image intensifier (detector) of a used x-ray apparatus via a fiducial device, see below, while intra-operatively, the phantom and an underlying object or target anatomy, e.g. the patient, can be tracked by an external pose tracking device such that the phantom can be placed anywhere on the target anatomy, wherein particularly the co-registration of multiple images of the same anatomy will be done via information provided by said tracker; alternatively, when the phantom is used independently from an external pose tracking device the relative fixation relationship between the phantom and the target anatomy has to be maintained in particular, which may be achieved by fixing the phantom onto the object or target anatomy by a fixation means such as a compression bandage system, for instance), wherein the phantom comprises a plurality of first calibration fiducials that are arranged in a first plane, generating at least one image (or a plurality of successive images) of said object by means of an x-ray apparatus, such that the at least one image contains projections of the object as well as projections of at least three first calibration fiducials, automatically detecting the positions of the projections of the at least three first calibration fiducials in said at least one image, and automatically computing for each of the 2D image coordinates of the positions of said projections of the at least three first calibration fiducials the corresponding 3D coordinates of said three first calibration fiducials in a local coordinate system of the phantom for automatically computing the projection matrix P (or at least an element thereof), i.e. the intrinsic projection parameters of the x-ray apparatus that can be expressed as intrinsic Matrix K and the extrinsic parameters (i.e. the position of the focal point of the x-ray apparatus with respect to the phantom), at least up to a scale factor, which is automatically done using preferably Eq. (1). In other words, the projection matrix P relates the 2D image coordinates $I_x$, $I_y$ of said first calibration fiducial's projections to the first calibration fiducial's 3D coordinates x, y, z according to $$\alpha[I_x, I_y, 1]^T = P[x,y,z,1]^T, \quad (1)$$

where $\alpha$ is a scale factor.

The calibration fiducials are preferably formed as spheres and are preferably made out of a material (e.g. steel) that generates a sufficient contrast when imaged by the x-ray apparatus such that the corresponding projections of the fiducials can be automatically detected in the generated images.

According to an aspect of the invention said at least three first calibration fiducials $\{M_i^1, M_i^2, M_i^3\}$, i=1, 2 or 3, are successively arranged along an associated (imaginary) line of said plane, wherein particularly the ratio $r_i = |M_i^1 M_i^2| / |M_i^2 M_i^3|$ is different from 1. Further, for the three triplets of fiducials, i=1, 2 or 3, said ratio is always unique, in order to allow for identifying which triplet of first calibration fiducials was actually detected. The first calibration fiducials (as well as further calibration fiducials) may particularly be arranged as described below.

According to an aspect of the invention said correspondence between the 2D image coordinates $I_x$, $I_y$ and the 3D coordinates in the local coordinate system installed on the mobile phantom is automatically established using a pinhole camera model for the projection of the x-ray apparatus with a reference position corresponding to extrinsic parameters $R_0$ and $T_0$ according to $$\alpha[I_x, I_y, 1]^T = K(R_0(R^x R^y R^z [x,y,z]^T + T) + T_0), \quad (2)$$

where $R^x$, $R^y$, $R^z$ and T are the rotation matrices around three axes, wherein particularly the z-axis (third axis) is in parallel with the view direction of the imaging apparatus (e.g. C-arm) at the reference position and the translation vector from an arbitrary acquisition position to the reference position, respectively, expressed in the local coordinates of the mobile phantom, wherein from the 3D coordinates of the at least three first calibration fiducials the intrinsic matrix K, $R_0$ and $T_0$ are determined once for the x-ray apparatus (pre-calibration).

Particularly, in order to determine the intrinsic matrix K and the pose $R_0$ and $T_0$ of the C-arm in the reference position with respect to the local coordinates of the mobile phantom (pre-calibration), all 16 calibration fiducials, i.e. the 7 (big) first calibration fiducials and the 9 (smaller) second and third calibration fiducials, are preferably used (see below). Since in the reference position, there is no object occluding the calibration fiducials and since this step is preferably done off-line for just one time, the correspondences between the projections of the calibration fiducials and said 3D coordinates of the calibration fiducials can be determined even interactively, if necessary. Thus, all 16 calibration fiducials are preferably used to compute K, $R_0$ and $T_0$. While intra-operatively, it is not permissible to determine the correspondences interactively due to a strict sterilization constraint.

To detect the phantom projection thereafter, when the x-ray apparatus, i.e. the axis of vision or viewing direction of the x-ray apparatus, is placed in the new position (or also in the reference position) a simulation-based method described in the following is preferably employed.

According thereto, the projections $IM_i^1$, $IM_i^2$, $IM_i^3$ of the at least three first calibration fiducials $M_i^1$, $M_i^2$, $M_i^3$ (preferably there a seven first calibration fiducials, such that three successive fiducials are arranged on three lines, see below, i.e. i=1, 2 or 3) are transformed and normalized by an e.g. 2D affine transformation such that the 2D image coordinates $I_x$, $I_y$ of the projections $IM_i^1$, $IM_i^2$, $IM_i^3$ of the at least three first calibration fiducials $M_i^1$, $M_i^2$, $M_i^3$ merely depend on rotations about a first axis (particularly the x-axis) and a second axis (particularly the y-axis) running orthogonal with respect to each other and with respect to a third axis (e.g. z-axis) forming the viewing direction of the x-ray apparatus in the reference position.

According to a further aspect of the invention, for finding the 3D coordinates in the local coordinate system installed on the mobile phantom, a look-up-table is generated in before-hand, which contains all the 2D Image coordinates $I_x$, $I_y$ of the detected, transformed and normalized projections of the at least three first calibration fiducials for different combinations of rotations of the 3D coordinates of said first calibration fiducials in the reference position about said first and second axis (e.g. Rotations $R^x$, $R^y$), which are particularly computed from Eq. (2) above. Particularly, the rotations may be increased/decreased in steps of a small angle, say e.g. 1°. Thus, having transformed and normalized the detected 2D image coordinates the look-up table is searched for the best match yielding the corresponding 3D coordinates. Preferably also look-up tables are computed for the other two triplets of fiducials $M_i^1$, $M_i^2$, $M_i^3$.

In order to be able to automatically compute the complete projection matrix P (i.e. the intrinsic and extrinsic parameters) up to said scale factor as stated in Eq. (1), N≥6 2D coordinates and corresponding 3D coordinates are needed. Therefore, at least projections of three further calibration fiducials are automatically detected, wherein at least one of said further fiducials is a second or third calibration fiducial being arranged in a second or third plane of the phantom running parallel to the first plane, wherein particularly the second or third fiducial(s) comprise a smaller volume than the first calibration fiducials.

Finally, the projection matrix P for the currently acquired image is computed, i.e. the projection parameters of the x-ray apparatus for the acquired image as well as the position of the x-ray device with respect to the phantom at the time when said image is acquired, using the 2D image coordinates $I_x$, $I_y$ of projections of the at least three first calibration fiducials and the at least three further calibration fiducials as well as the corresponding 3D coordinates x, y, z of the respective calibration fiducials.

According to a further aspect of the invention, the mobile phantom is further automatically tracked e.g. by means of an external pose tracking system. Then, it is possible to transform this position from the phantom coordinate system to any other reference coordinate system.

Furthermore, the problem underlying the present invention is solved by a computer program product, which is designed to conduct at least the third and the fourth step of the method according to the present invention (eventually also the other steps), i.e., detecting projections of at least three first calibration fiducials in at least one image, and establishing a correspondence between the 2D image coordinates of said projections of the at least three first calibration fiducials and the 3D coordinates of said at least three first calibration fiducials in a local coordinate system of a phantom for computing the projection matrix P or at least an element of the projection matrix P at least up to a scale factor $\alpha$, which projection matrix relates said 2D image coordinates $I_x$, $I_y$ to said corresponding 3D coordinates x, y, z in a local coordinate system of the phantom according to $\alpha[I_x, I_y, 1]^T = P[x,y,z,1]^T$ (see also above), when running on a computer or loaded into a computer, as well as eventually also one of the other steps of the method according to the present invention.

Furthermore, the problem underlying the present invention is solved by a mobile phantom for an x-ray apparatus, particularly for use in the phantom detection method as described above.

According thereto, the phantom is a mobile phantom that can be manually displaced, wherein the phantom comprises three first calibration fiducials being arranged along a first line, wherein particularly the phantom comprises three further first calibration fiducials being arranged on a third line running parallel to the first line, and wherein particularly the phantom comprises a further first calibration fiducial arranged on a second line running from a first calibration fiducial that is arranged between two first calibration fiducials on the first line to a first calibration fiducial that is arranged between two first calibration fiducials on the third line, wherein particularly the second line runs perpendicular to the first and the third line, such that also three first calibration fiducials are arranged on the second line, wherein particularly the seven fiducials are all arranged in a first plane, and wherein particularly the three ratios $r_i=|M_i^1M_i^2|/|M_i^2M_i^3|$ are different from each other, particularly different from 1, and wherein particularly the phantom comprises second calibration fiducials arranged in a second plane running parallel to the first plane, and wherein particularly the phantom comprises third calibration fiducials being arranged in a third plane running parallel to the first and second plane, wherein particularly the first calibration fiducials comprise a larger diameter than the second and/or third calibration fiducials, which may have the same diameter. Further, said lines are preferably imaginary lines, i.e., there must be no corresponding structure on the phantom like a groove or painted line.

Preferably, the carrier is formed out of a (e.g. clear) plastic material and preferably comprises a plate extending along the first plane, into which the first fiducials are preferably embedded. The (first, second and third) calibration fiducials are preferably formed as spheres made out of a metal, particularly steel.

Further, the plate preferably comprises two opposing (parallel) boundary regions, wherein a side wall protrudes from each of the boundary regions via which the phantom can rest on the target anatomy or the image detector (e.g. in the reference position) such that the plate (first plane) runs across the viewing direction of the x-ray apparatus (z-axis of the local coordinate system of the phantom).

Preferably, coming from the plate, each sidewall comprises a first step and a second step below the first step, each of the steps extending parallel to the respective boundary region, wherein the first steps extend along the second plane and wherein the third steps extend along the third plane.

Now, the second calibration fiducials are preferably embedded into the second steps, while the third calibration fiducials are preferably embedded into the third steps.

In case the x-ray apparatus that is employed for the phantom detection method according to the invention comprises a flat panel detector that shows no distortions of the detected image the following additional method steps need not to be performed.

However, when necessary, a statistical model for correcting distortions (e.g. due to the earth magnetic field) of intra-operatively generated images can be automatically computed beforehand and this model can then be used in the phantom detection method to automatically correct for distortions of the generated images although the following method can also be employed in other contexts, particularly without the mobile phantom presented here.

This further method according to the invention, which may also be incorporated into the above described phantom detection method, requires the steps of (before acquiring e.g. intra-operative images of said object or target anatomy): rigidly attaching a fiducial device comprising a plurality of fiducials to an image detector of an x-ray apparatus, which image detector is configured to detect x-rays (photons) generated by an x-ray generating means opposing said image detector along a viewing direction of the x-ray apparatus, wherein particularly the image detector is an image intensifier being configured to convert x-ray photons into visible photons which can then be captured by a camera in order to generate an image (or a stream of images) of the object.

Preferably, said fiducial device comprises a plate carrying said fiducials, wherein the latter are arranged in a single extension plane along which the plate extends, which extension plane is particularly oriented perpendicular to the viewing direction (optical axis) of the x-ray apparatus.

Further, said fiducials are preferably arranged on (fictitious) lattice points of a rectangular, particularly square lattice (in said single extension plane).

In order to provide a statistical model of the image distortion pattern that can be used to undo the distortions, said viewing direction (e.g. C-arm) is positioned in different orientations with respect to the earth magnetic field, and a model building image $I^n$, where $n=1, \ldots, N$ labels the individual model building image $I^n$, is generated by means of the x-ray apparatus for each of said orientations containing projections of all fiducials embedded into the plate.

Then, the positions $\{P_n^i\}$ of the projections of the fiducials in the respective model building image $I^n$, where i labels the fiducials and n the respective model building image, are preferably automatically detected.

Next, a displacement vector $D_n=[D^1_{n,x},D^1_{n,y}, \ldots, D^{N_i}_{n,x},D^{N_i}_{n,y}]^T$ is automatically computed for each model building image $I^n$ containing the vectors $D_n^i=[D^i_{n,x},D^i_{n,y}]^T$ that extend from the nominal (undistorted) position $\bar{P}^i$ of the respective fiducial to the detected position $P_n^i$ of the projection of said fiducial, and wherein particularly a mean displacement map $M_D$ as the average of all displacement vectors $\{D_n\}$ is automatically computed and subtracted from each displacement vector $D_n$ in order to apply a principal component analysis to the variation of the displacement vectors $D_n$ yielding the eigen displacement maps $\{P_D^i\}$ and particularly the eigen values $\{\lambda^i\}$ of said variation, thus yielding a statistical model for the distortions of the fiducial projections due to the earth magnetic field and eventually other (local) influences.

According to an aspect of the invention, a part, particularly a part of said plate, comprising some of the fiducials is removed from said device (plate) for generating the actual images of the object/target anatomy (e.g. intra-operative) so that the plate comprises a recess being free of fiducials. Accordingly, when an image is now generated by means of the x-ray apparatus, the image comprises a corresponding region being free from projections of the fiducials carried by said removed part as well as a further (boundary) region containing projections of remaining boundary fiducials of the device.

With said part being removed from the fiducial device at least one image (or a plurality of images) of said object (target anatomy) is generated by means of the x-ray apparatus such that the at least one image contains projections of said object as well as projections of the boundary fiducials, and particularly the projections of the at least three first calibration fiducials (and eventually further calibration fiducials).

Now, for instantiation of the derived statistical model of the variations of the displacement vectors, the projections of the boundary fiducials are automatically detected in the at least one image, and the corresponding boundary displacement vector $B_n=[B^1_{n,x},B^1_{n,y}, \ldots, B^{N'}_{n,x},B^{N'}_{n,y}]^T$, where N' is the number of boundary fiducials, which contains the individual vectors $B_n^i=[B^i_{n,x},B^i_{n,y}]^T$ extending from the nominal (undistorted) position of the respective boundary fiducial i to the detected position of the projection of said boundary fiducial I, is automatically computed, wherein a linear combination $M_D+\Sigma_i b_i P_D^i$ (summation over i, i.e., over a finite number of $P_D^i$'s), where $M_D$ is the pre-computed mean displacement map and $\{P_D^i\}$ are the pre-computed eigen displacement maps is automatically fitted to the boundary displacement vector in order to get an estimate for the displacement vector of all fiducials, i.e. also for the empty region.

Finally, the at least one image is undistorted (de-warped) using the automatically estimated displacement vector $D_n$ of the at least one image by undoing the distortion according to the estimated displacement vector $D_n$, thus yielding the undistorted image (de-warping). The regions between the fiducials can be interpolated with help of polynomials (preferably fifth-order).

Finally, the fiducial projections can be automatically inpainted from the respective image.

Further, the problem underlying the present invention is solved by a computer program product or by a computer program that are both designed to conduct at least the fourth, fifth and sixth step of the method according to the present invention relating to the statistical model.

(eventually also the other steps), i.e., detecting the positions $\{P^i_n\}$ of the projections of fiducials in a respective model building image $\{I^n\}$, computing a displacement vector $D_n = [D^1_{n,x}, D^1_{n,y}, \ldots, D^{N_t}_{n,x}, D^{N_t}_{n,y}]^T$ for each acquired model building image $I^n$, wherein the vectors $D^i_n = [D^i_{n,x}, D^i_{n,y}]^T$ extend from the nominal (undistorted) position $\bar{P}^i$ of the respective fiducial i to the detected position $P^i_n$ of the projection of said fiducial i, and wherein particularly a mean displacement map $M_D$ as the average of all displacement vectors $D_n$ is computed and subtracted from each displacement vector $D_n$ and a principal component analysis is applied to the resulting variation of the displacement vectors $D_n$ in order to compute eigen displacement maps $\{P^i_D\}$ and particularly eigen values $\{\lambda^i\}$ of said variation, when loaded into a computer (e.g. memory of the computer) and/or running on the computer, as well as eventually also one of the steps of the method relating to the statistical model. The computer program (e.g. of the computer program product) may be stored on a medium that can be read by a computer; the computer program may also be downloadable from a server.

According to a further aspect of the invention, a fiducial device is proposed.

The fiducial device is designed to be fixed to an image detector, particularly an image intensifier of an x-ray apparatus, wherein the fiducial device comprises a plate carrying said fiducials, particularly in a single extension plane along which the plate extends.

Preferably, said fiducials are arranged on lattice points of a rectangular, particularly square lattice (in said single extension plane), wherein the plate preferably comprises a part containing some of the fiducials, which part is designed to be released from the plate leaving an (e.g. square or rectangular) recess in the plate without fiducials such that an image acquired by means of the x-ray apparatus when said part is released from the plate comprises a region corresponding to the recess being free from projections of the fiducials of said part as well as projections of remaining fiducials (so called boundary fiducials) arranged along the recess.

The plate may comprise a rigid frame that may be made out of a metal like steel or aluminum and a plate element attached thereto, which is preferably made out of a plastic material and to which the fiducials are fixed. The fiducials are preferably made out of a metal (e.g. steel) and may comprise a cross-shaped cross-sectional contour in said extension plane.

BRIEF DESCRIPTION OF THE DRAWINGS

Further features and advantages of the invention shall be described by means of detailed descriptions of embodiments with reference to the Figures, wherein.

DETAILED DESCRIPTION

The present invention particularly relates to an x-ray apparatus (e.g. C-arm) calibration approach that is based on a fiducial device 10, also denoted as distortion correction plate, having fiducials 100 arranged in a single extension plane (cf. FIGS. 1 and 2) as well as a mobile phantom 20 (cf. FIG. 6) that can be placed to anywhere close to the patient anatomy being imaged.

Figure 3:
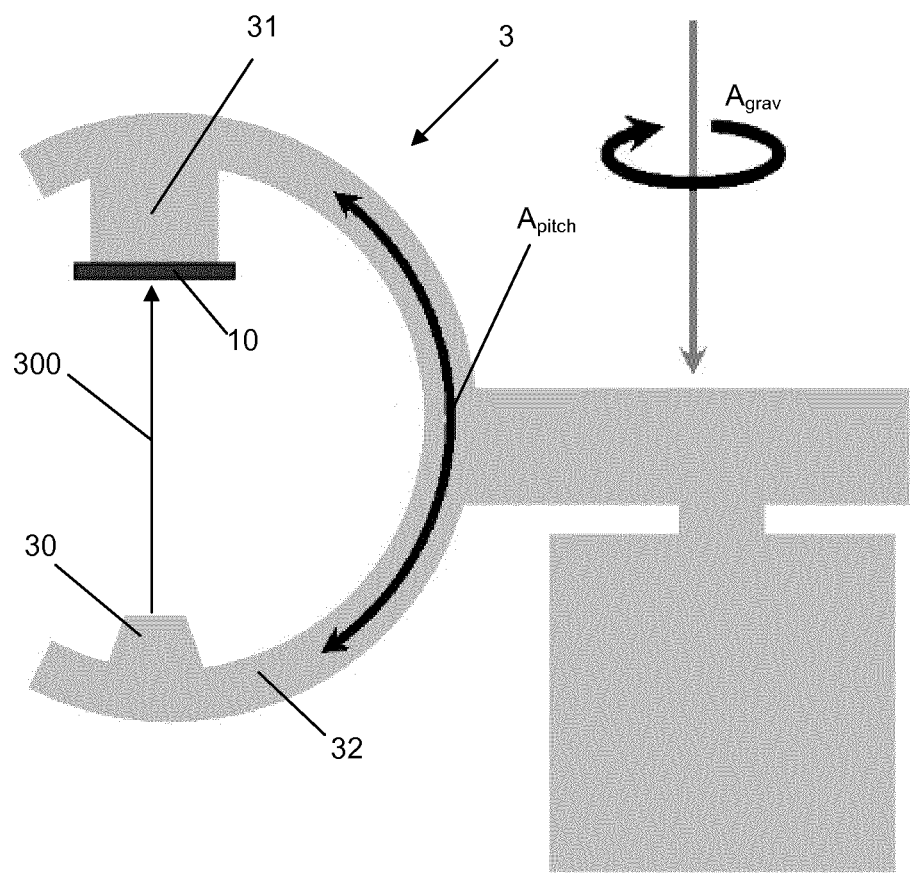
FIG. 3 shows a schematical side view of an x-ray apparatus (C-arm), wherein for building the statistical model of the image distortion pattern (before image calibration), an image for each considered orientation with respect to the axes $A_{grav}$ and $A_{pitch}$ is taken from all fiducials of the fiducial device attached to the x-ray generating means.

Particularly, the invention relates to calibration and tracking of digital x-ray apparatuses 3 (cf. FIG. 3) such as those used in conventional computer tomographs or cone-beam computer tomographs as well as those equipped with C-arm and O-arm type stands. According to FIG. 3 such an x-ray apparatus 3 comprises an x-ray generating means 30 for generating x-rays as well as an image detector 31 for detecting the x-rays, which opposes the x-ray generating means 30 along a viewing direction 300 of the x-ray apparatus 3, along which the x-rays impinge on the object to be imaged and the detector 31. Said detector 31 may be an image intensifier 31 that is adapted to convert the x-rays into visible light from which an image can be generated by the x-ray apparatus (e.g. via a camera like a CCD camera). The x-ray generating means 30 and the image intensifier 31 are rigidly connected by a C-shaped arm 32 that can be tilted around a pitch axis $A_{pitch}$ and pivoted about a vertical axis $A_{grav}$ as indicated in FIG. 3 such that the viewing direction can be spatially adjusted (with respect to its orientation and position in space).

Figure 9:
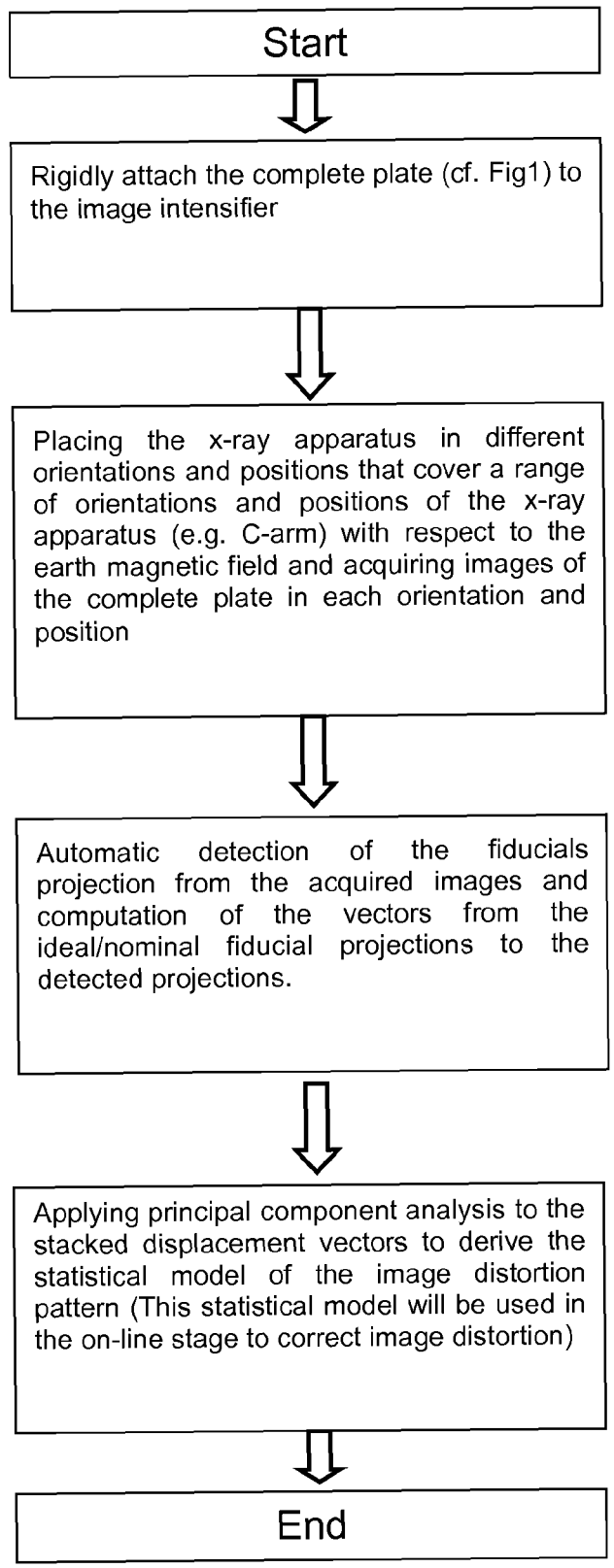
FIG. 9 a possible flow chart of the method for building a statistical model for image distortion correction.
Figure 10:
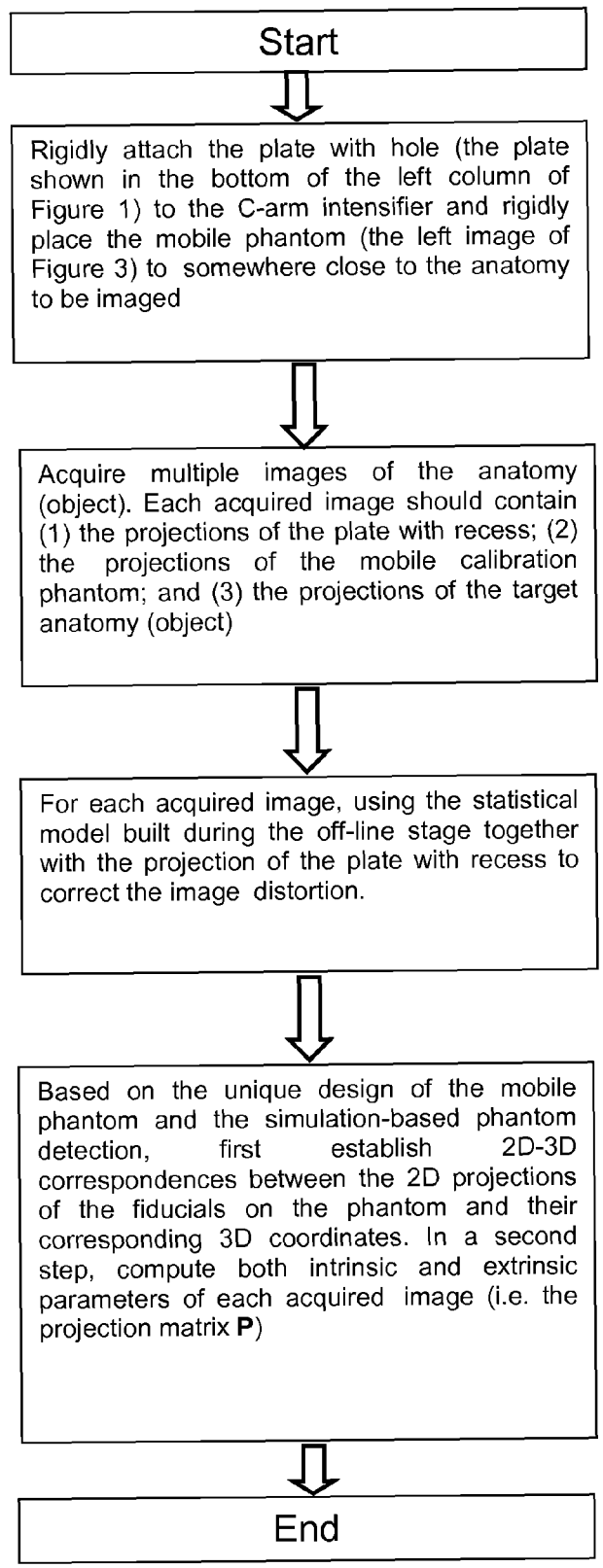
FIG. 10 a possible flow chart of the method for phantom detection (with prior image distortion correction).

In particular the method according to the invention is essentially based on (1) building a statistical model of the x-ray image distortion models before the calibration and using the resultant statistical model to correct the X-ray image distortion during the calibration (cf. flow chart according to FIG. 9), and/or (2) a phantom and a phantom detection method to obtain the projection parameters of the X-ray device for the acquired image as well as the position of the X-ray device with respect to the phantom at the time when the image is acquired (cf. flow chart according to FIG. 10).

It is possible that for a newly introduced digital X-ray apparatus where a flat panel detector is used, there is no need to do the step (1).

In such a situation, the phantom and the phantom detection method still can be used to obtain the projection parameters of the X-ray device for the acquired image as well as the position of the X-ray device at the time with respect to the phantom when the image is acquired. By tracking the phantom with an external pose tracking system, it is then possible to transform this position from the phantom coordinate system to any other reference coordinate system, although such a transformation is not necessary for certain applications.

Further, the method for building the statistical model/image distortion correction can be performed independently with respect to the phantom detection method.

Now, for building the statistical model, the fiducial device 10 is used. As all the fiducials 100 are arranged in one (extension) plane, the reduction of imaging space due to the distortion correction plate 10 is negligible compared to other calibration cages used in most existing systems, leading to a minimization of interference with the patient anatomy being imaged.

Figure 1:
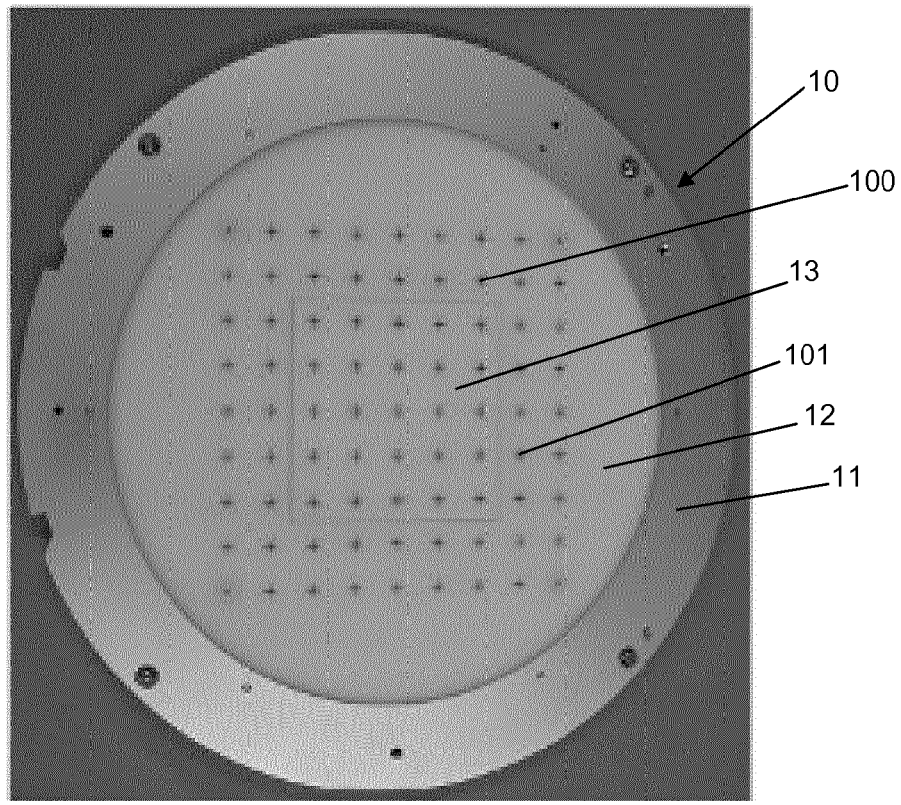
FIG. 1 shows the fiducial device comprising a plate from which a part that is releasably fastened to the plate can be removed.
Figure 2:
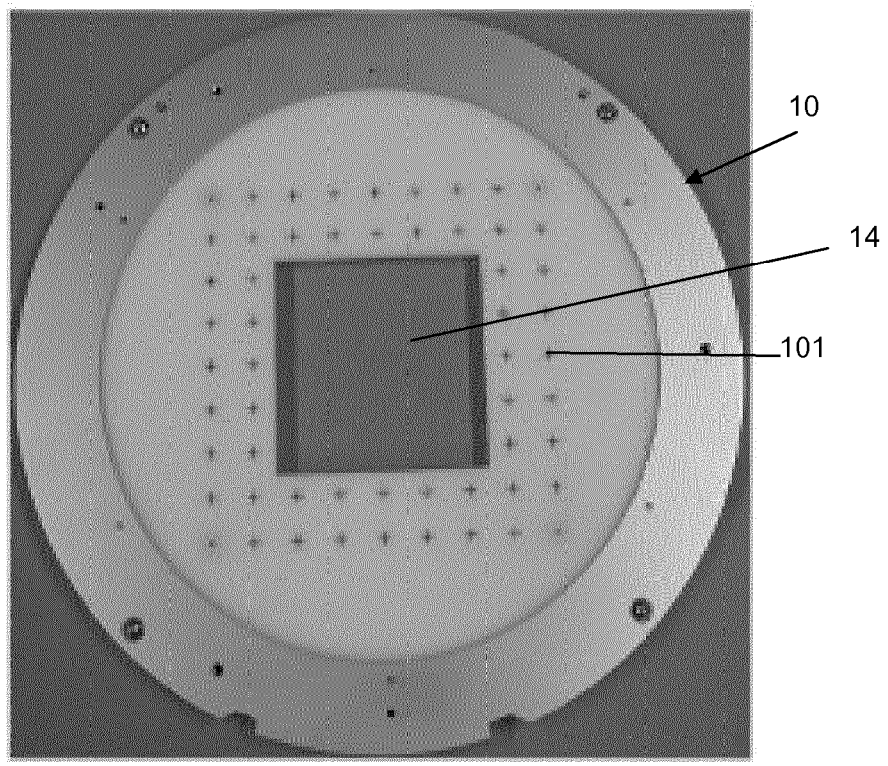
FIG. 2 shows the fiducial device according to FIG. 1 without said part.

As can be seen from FIGS. 1 and 2 the individual fiducials 100 may be cross-shaped and arranged on the lattice points of a (fictitious) square lattice. Such a grid allows one to easily track the distortions of the image due to the earth magnetic field and eventually other influences. Preferably, the fiducial device 10 comprises 77 fiducials 100 which are embedded into a particularly circular plate 11, 12 of the device 10, which plate 11, 12 extends along said extension plane. The plate 11, 12 may comprise an outer (circular) rigid frame 11 for fixing the fiducial device 10 to an image detector (intensifier) 31 of an x-ray apparatus 3, which frame 11 holds a central plate element 12, which carries the fiducials 100. A central (square) part 14 of the plate 11, 12, namely of the central plate element 12, is designed to be detachable from the fiducial device 10, so that a number of central fiducials 100 embedded into said part can be removed from the plate 10 leaving a recess (hole) 14 in the plate 11, 12. Thus, when an image is taken from the fiducial device 10 with recess 14, only projections of the boundary fiducials 101 are present in the image.

Building the statistical model is only needed to be done off-line one time for a certain x-ray apparatus (C-arm) 3. At this stage, the central part 13 of the fiducial device 10 will be mounted to have a complete fiducial device as shown in FIG. 1 and the complete fiducial device 10 will be rigidly attached to the image intensifier 31 as shown in FIG. 3 such that the viewing direction 300 is particularly normal to the extension plane of the fiducial device 10. Thus if no distortion would be present, the projections of the fiducials would form the same square lattice (grid) as the fiducials (up to a scale factor).

By placing now the C-arm 32 (or viewing direction 300) in different orientations and acquiring images of the fiducial device 10, i.e. of its fiducials extending along a single extension plane, a statistical model of the C-arm image distortion pattern can be established from fiducial projections detected from all acquired images. In detail, the individual imaging positions are selected by rotating the C-arm 32 (or viewing direction 300) around said axes $A_{grav}$ and $A_{pitch}$ while keeping the roll angle of the C-arm at 0 degree as shown in FIG. 3 in order to estimate the influence of the earth magnetic field on the image distortion. The first rotation $Rot_{Grav}$ about the Axis $A_{grav}$ is around the gravity direction, i.e. rotating the whole C-arm 32 horizontally to reveal the influence of the magnetic field of the earth, and the sampling interval is preferably 20°. The second rotation is the pitch rotation of the C-arm 32 and the sampling interval is also preferably 20°. Additionally three more images are generated resulting in 383 model building images in total.

Given these model building images $\{I^n\}$; n=1, 2, ..., N=383, a cross-correlation based template matching is used to automatically detect the projections of all the fiducials from each image In and the detected fiducial positions $\{P_i^n\}$, i=1, 2, ..., 77, n=1, 2, ..., 383, are saved for the model building. The statistical model is then built as follows:

For each model building image $I^n$, the displacement vector $D_n = [D^1_{n,x}, D^1_{n,y}, \ldots, D^{77}_{n,x}, D^{77}_{n,y}]^T$ is computed, where $D^i_n = [D^i_{n,x}, D^i_{n,y}]^T$ are defined as the vectors starting from the ideal/nominal fiducial projections $\bar{P}^i$, which are determined from the physical geometry of the fiducial layout 100, to the detected fiducial projection $P^i_n$.

Taking the displacement vectors $\{D_n\}$, n=1, 2, ..., 383 as the input, the mean displacement map $M_D$ is at first automatically computed as the average of all displacement vectors. The mean displacement map is then automatically subtracted from each displacement vector before a principal component analysis[10] is performed on the variation of the displacement vectors to compute the eigen displacement maps $\{P^i_D\}$ and the eigen values $\{\lambda^i\}$ of the variation. Then, any displacement map can be parameterized by the statistical model with much less number of parameters.

Figure 4:
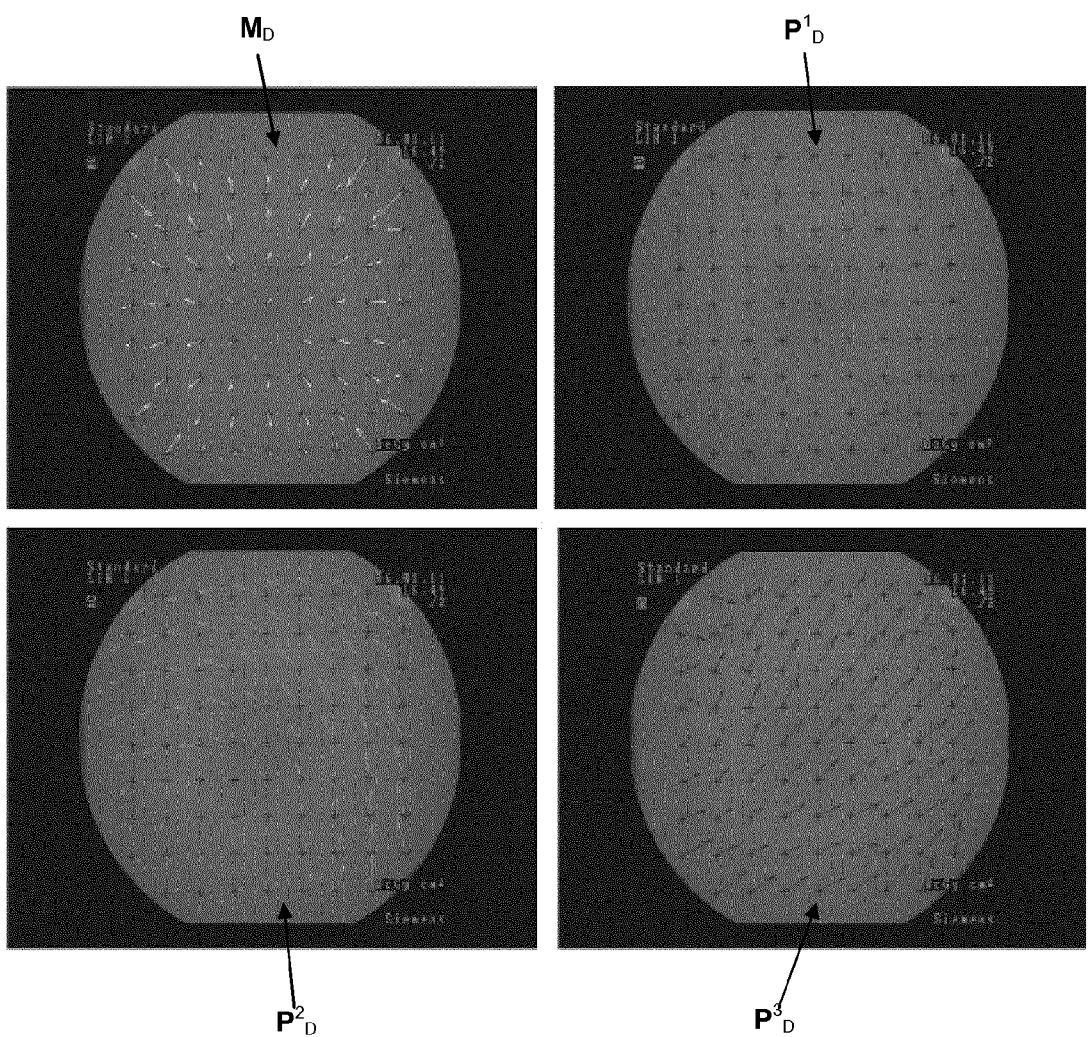
FIG. 4 shows a statistical model of an image distortion pattern of an x-ray device, i.e., the mean displacement map (top left), and the first three eigen displacement maps (top right: 1st; bottom left: 2nd, bottom right: 3rd eigen displacement map) computed by means of PCA. During image acquisition, such a statistical model of the distortion pattern will be used together with the acquired images of the plate with recess (hole) to first estimate the image distortion and then to correct the image distortion by an image dewarping process.

One can show that over 98% of the variations can be explained by the first 3 eigen displacement maps $P^1_D, P^2_D, P^3_D$ of the model as depicted in FIG. 4. The top left panel of FIG. 4 shows the mean displacement map $M_D$.

Intra-operatively, when image distortion correction is needed, the central part 13 of the image distortion correction plate (fiducial device) 10 will be removed before it is attached to the image intensifier 31. Thus, only the boundary fiducials 101 will be visible in an intra-operatively acquired image. The projections of these boundary fiducials 101 can be robustly automatically detected by using the same cross-correlation based template matching as mentioned before such that the displacement vectors of these fiducials 101 with respect to the corresponding nominal fiducial projections can be precisely estimated. The estimated displacement vectors of these boundary fiducials are then used to instantiate the statistical model of the x-ray apparatus (C-arm) image distortion pattern, leading to the extrapolation of the displacement vectors for those missing fiducials at the central part 13 of the plate 11, 12 of the fiducial device 10. Preferably, the extrapolation is done based on the statistical instantiation method proposed by Rajamani et al.[11], which describes a Mahalanobis distance weighted least square fit of a linear combination of the above described eigen displacement maps to the displacement vector of the boundary fiducials.

Thus, the method according to the invention advantageously allows one to use the sparse fiducials around the border of the plate 11, 12 that are visible in each intra-operatively acquired image for estimating the projection locations of the missing fiducials by combining the detected boundary fiducial projections with the statistical model of the image distortion pattern.

Figure 5:
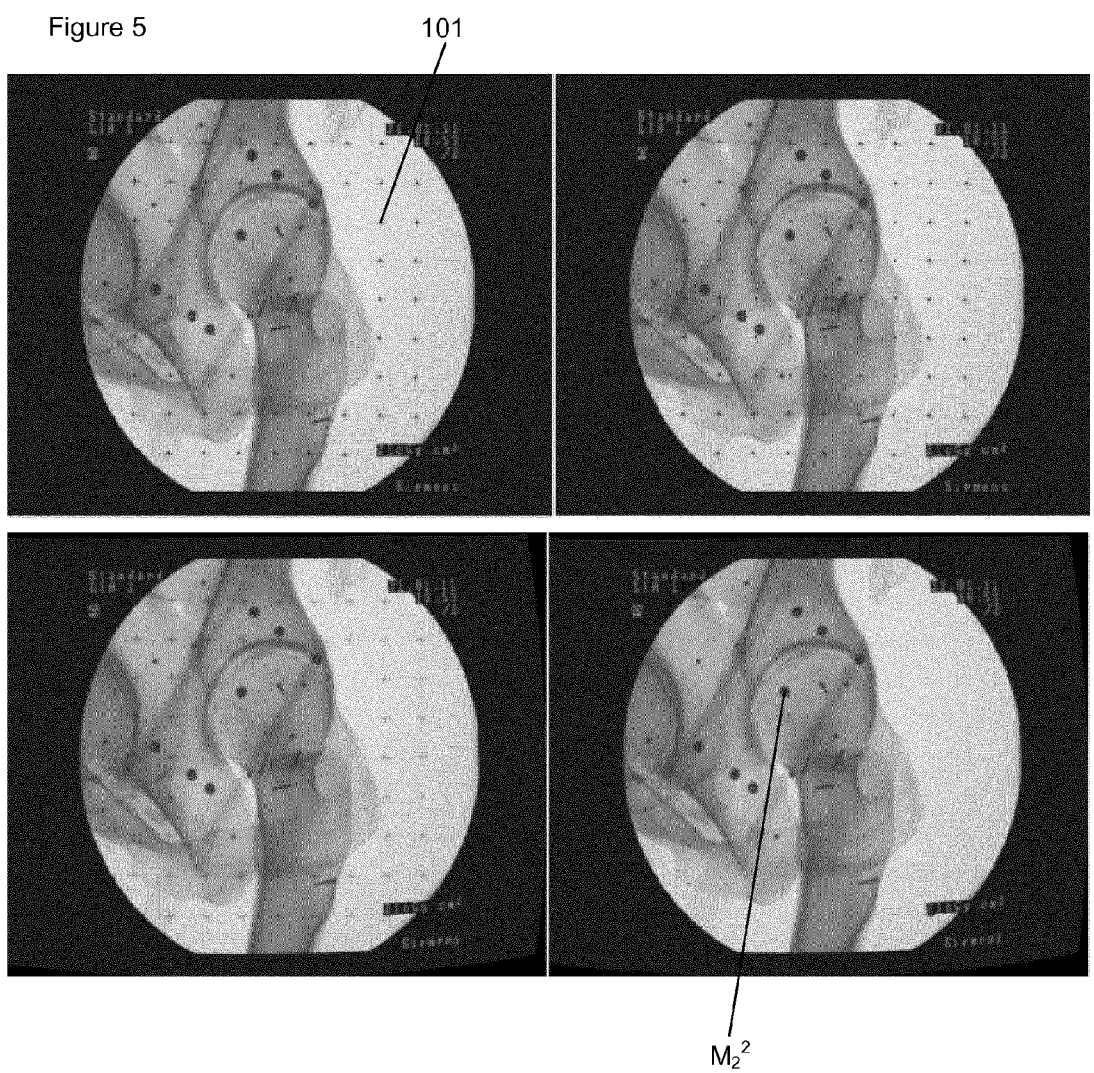
FIG. 5 shows an example for a statistical model based image distortion correction pipeline: detection of boundary fiducial projection from the acquired image of the plate with recess (hole) (top left), estimation the statistical model of the image distortion pattern (top right), image distortion correction (bottom left) and fiducial projection inpainting (bottom right)

Based on the resulting displacement vector of all fiducials, the image is then undistorted using a fifth order polynomial-based approach. Moreover, the fiducial projections are preferably inpainted from the image with the method implemented in OpenCV library[12]. An example for the above-described statistical model based image distortion correction is shown in FIG. 5.

In order to calibrate each intra-operatively acquired image, one needs to compute both the intrinsic and the extrinsic parameters of the image. This is particularly achieved in the present approach by means a mobile phantom as shown in FIG. 6

There are totally 16 sphere-shaped calibration fiducials embedded in this phantom 20, namely 7 big first calibration fiducials $\{M_i^1, M_i^2, M_i^3\}$, i=1, 2, 3, having a diameter of preferably 5.0 mm and 9 small second and third calibration fiducials 201, 202 having a diameter of 2.5 mm. The 16 calibration fiducials $\{M_i^1, M_i^2, M_i^3\}$, 201, 202 are arranged in three different planes: all 7 big first calibration fiducials $\{M_i^1, M_i^2, M_i^3\}$ are placed in a first plane and the remaining 9 small second and third calibration fiducials 201, 202 are distributed in a parallel second and a parallel third plane, wherein each of the three planes is different from the other planes.

Figure 6:
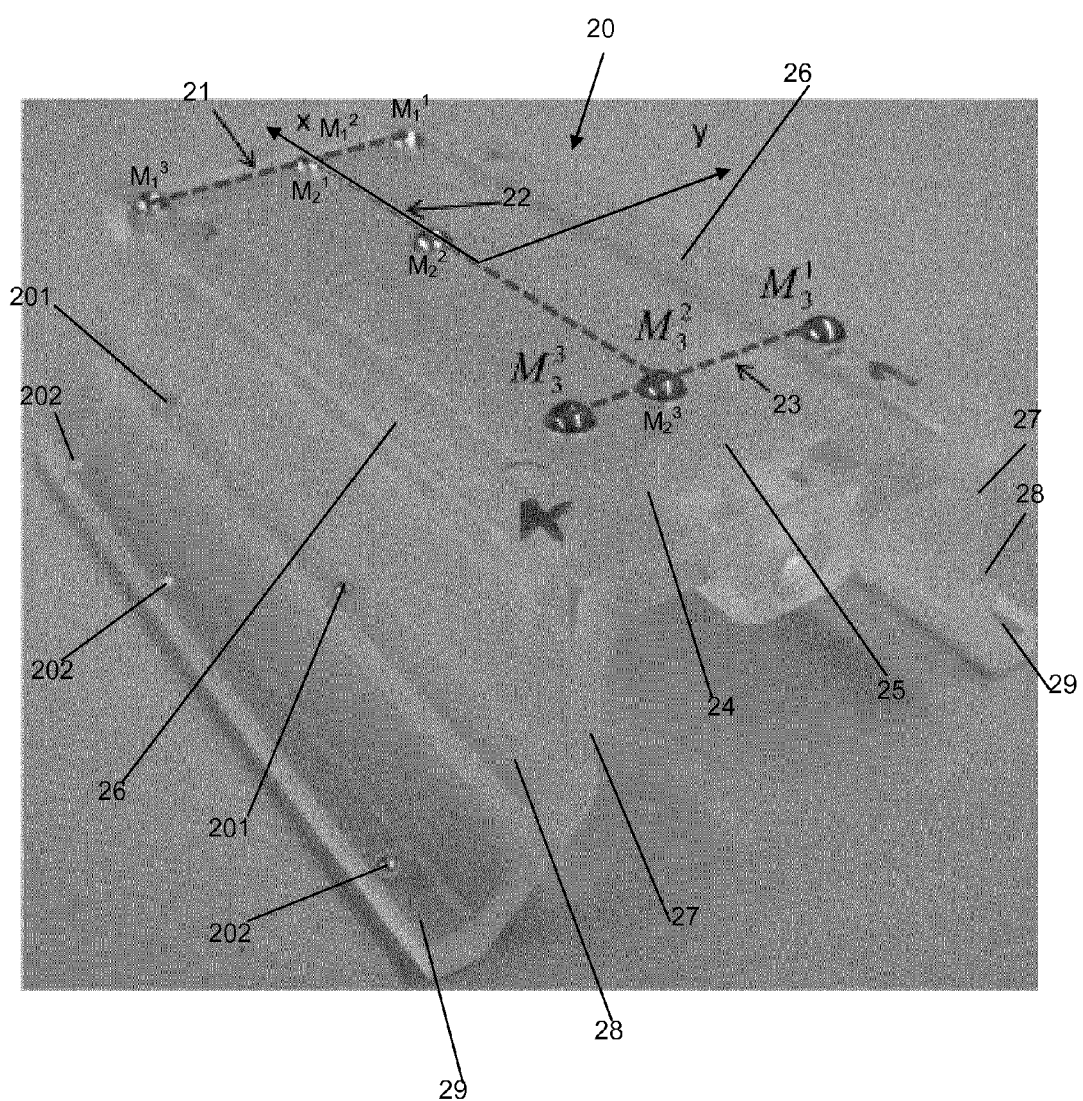
FIG. 6 shows a perspective view of a mobile phantom with calibration fiducials.

Furthermore, the 7 big calibration fiducials $\{M_i^1, M_i^2, M_i^3\}$ are arranged to form three line patterns as shown in FIG. 6. Every line pattern consists of three first calibration fiducials $\{M_i^1, M_i^2, M_i^3\}$, i=1, 2, 3 with different ratios $\{r_i=|M_i^1 M_i^2|/|M_i^2 M_i^3|\}$. The exact ratio for each line 21, 22, 23 is used below to identify which line pattern has been successfully detected.

Particularly, the phantom 20 comprises three first calibration fiducials $M_1^1, M_1^2, M_1^3$ being arranged along a first line 21, wherein particularly the phantom comprises three further first calibration fiducials $M_3^1, M_3^2, M_3^3$ being arranged on a further (third) line 23 running parallel to the first line 21, and wherein particularly the phantom 20 comprises a further first calibration fiducial $M_2^2$ arranged on a further (second) line 22 running from a first calibration fiducial $M_1^2$ that is arranged between the two first calibration fiducials $M_1^1, M_1^3$ on the first line 21 to a first calibration fiducial $M_3^2$ that is arranged between two first calibration fiducials $M_3^1, M_3^3$ on the third line 23, wherein particularly the second line 22 runs perpendicular to the first 21 and the third line 23 such that also three first calibration fiducials $M_2^1, M_2^2, M_2^3$ are arranged on the second line 22.

Preferably, the phantom 20 comprises a carrier 24 that is formed out of a (e.g. clear) plastic material and preferably comprises a plate 25 extending along the first plane, into which the first calibration fiducials are preferably embedded. Said plate 25 comprises two parallel boundary regions 26, wherein a side wall 27 protrudes from each of the boundary regions 26 via which the phantom 20 can rest on the target anatomy or the image detector (e.g. in the reference position) 31 such that the plate (first plane) 25 runs across the viewing direction 300 of the x-ray apparatus 3 (z-axis of the local coordinate system of the phantom 20, cf. FIG. 7).

Each side wall 27 comprises a first step 28 into which the second calibration fiducials 201 are embedded, which first steps 28 extend along said second plane, as well as a second step 29 into which the third calibration fiducials 202 are embedded, which second steps 29 extend along said third plane.

After the distortion of an intra-operatively acquired image is corrected, a sequence of automatic image processing operations may be applied to the image. As those calibration fiducials $\{M_i^1, M_i^2, M_i^3\}$, 201, 202 are made from a metal (steel), a simple threshold-based method is preferably first used to segment the image. Connected-component labeling is then applied to the binary image to extract a set of separated regions. Morphology analysis is further preferably applied to each label connected-component to extract two types of regions: candidate regions from (big) first calibration fiducial projections and candidate regions from small calibration fiducial projections. The centers of these candidate regions are regarded as projections of the center of a potential calibration fiducial. Due to background clutter, it is feasible that some of the candidate projections are outliers and that one may miss some of the true fiducial projections. Furthermore, to calculate both the intrinsic and the extrinsic parameters, we have to detect the phantom 20 from the image. Here, phantom detection means to establish the correspondences between the detected 2D fiducial projection centers and their associated 3D coordinates x,y,z in the local coordinate system of the phantom 20.

For this purpose, a robust simulation-based approach is utilized. The pre-condition to use this method to build the correspondences is that one of the three line patterns of first calibration fiducials $M_i^1, M_i^2, M_i^3$, i=1, 2 or 3, has been successfully detected. Due to the fact that these line patterns are defined by (big) first calibration fiducials, the chance to missing all three line patterns is rare.

We model the C-arm projection using a pin-hole camera.

$$\alpha[I_x, I_y, 1]^T = K(R[x, y, z]^T + T) = P[x, y, z, 1]^T \quad (1)$$

where $\alpha$ is a scale factor, K is the intrinsic calibration matrix, R and T are the extrinsic rotation matrix and translational vector, respectively. Both the intrinsic and the extrinsic projection parameters K, R and T can be combined into a 3-by-4 projection matrix P in the local coordinate system established on the mobile phantom.

Figure 7:
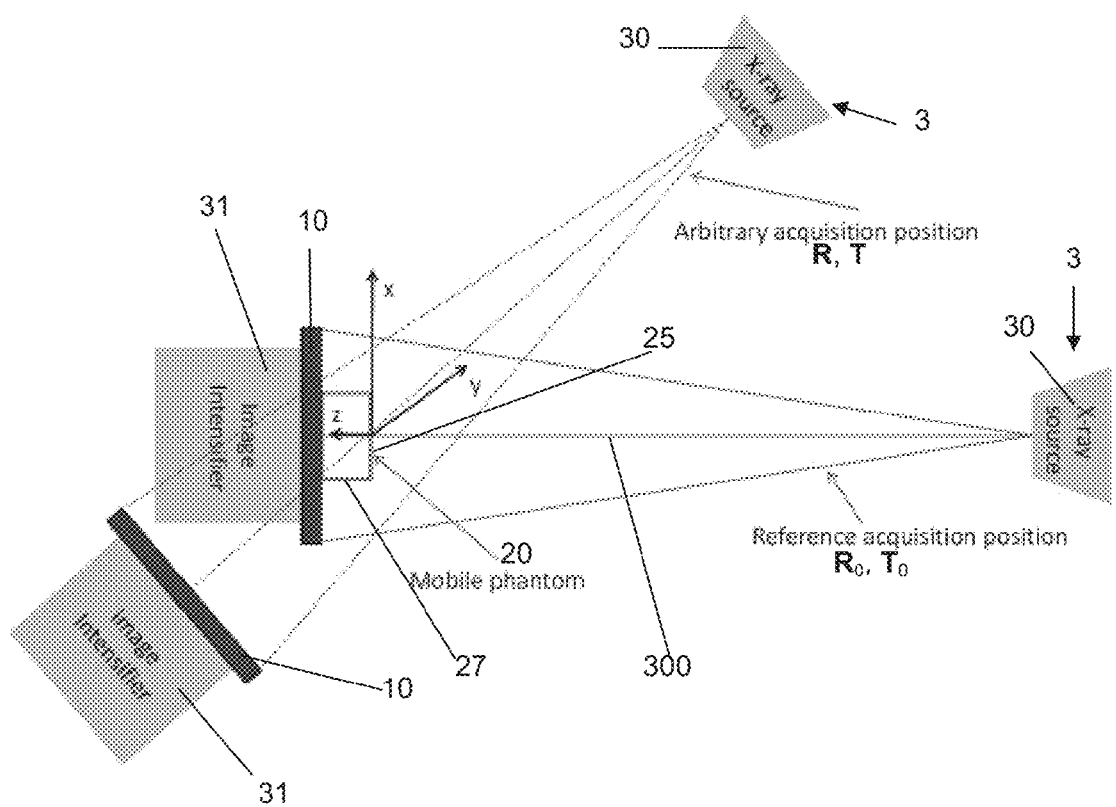
FIG. 7 shows a schematic view of the look-up table based method for 2D-3D correspondence establishment.

The idea behind the simulation-based method is to do a pre-calibration to compute both the intrinsic matrix K as well as the extrinsic parameters $R_0$ and $T_0$ of the C-arm in a reference position from Eq. (2) as shown in FIG. 7. According thereto, the viewing direction 300 of the x-ray apparatus 3 aligns with the z-axis of the local coordinate system of the phantom 20, which is fixed via its side walls 27 to the fiducial device 10 such that the first plane of the phantom 20 (i.e. the plate 25 of the carrier 24) extends perpendicular to the viewing direction 300 and to the plate 11, 12 of the fiducial device 10. Thus, in the reference position the plane spanned by the x- and y-axis of the local coordinate system of the phantom extends parallel to the plate 11, 12. The origin of the local coordinate system is preferably arranged in the center of the plate 25 of the carrier 24 of the phantom 20.

Then, assuming that the intrinsic matrix K is not changed from one image to another (we only use this assumption for building the correspondences), the projection of the x-ray apparatus 3 (C-arm) at any other position with respect to the phantom 20 can be expressed as $$\alpha[I_x, I_y, 1]^T = K(R_0(R^x R^y R^z [x,y,z]^T + T) + T_0) \quad (2)$$

where $R^x$, $R^y$, $R^z$ and T are the rotation matrices around three axes (assuming the z-axis is in parallel with the view direction of the C-arm at the reference position, see FIG. 7) and the translation vector from an arbitrary acquisition position to the reference position, respectively, expressed in the local coordinate x, y, z of the mobile phantom 20. To detect the phantom projection when the x-ray apparatus (C-arm) 3 is placed in a new position (cf. FIG. 7), the simulation-based approach consists of two steps.

Firstly, one wants to get rid of the influence of the parameters $R^z$, $\alpha$, and T on the phantom detection by normalizing the image acquired at the new position (arbitrary acquisition position in FIG. 7) as follows. Assuming that one knows the correspondences of fiducials on one line pattern, which is defined by 3 landmarks $M^1$, $M^2$, $M^3$ with their correspondent projections at $IM^1$, $IM^2$, $IM^3$, one can define a 2D coordinate system based on $IM^1$, $IM^2$, $IM^3$, whose origin 0 is located at $(IM^1+IM^2)/2$ and the x-axis is defined along the direction origin $0 \to IM^3$. Accordingly a 2D affine transformation $T_{normalize}$ can be computed to automatically transform this line pattern based coordinate system to a standard 2D coordinate system with its origin at (0, 0) and x-axis along direction (1, 0) and at the same time to normalize the length of the vector $IM^1 \to IM^3$ to 1. By applying $T_{normalize}$ to all the fiducial projections, it can be observed that for a pair of fixed $R^x$ and $R^y$, we can get the same normalized image no matter how the other parameters $R^z$, $\alpha$, and T are changed because the influence of these parameters is just to translate, rotate, and scale the fiducial projections, which can be compensated by the normalization operation. Therefore, the fiducial projections after the normalization will only depend on the rotational matrices $R^x$ and $R^y$.

Figure 8:
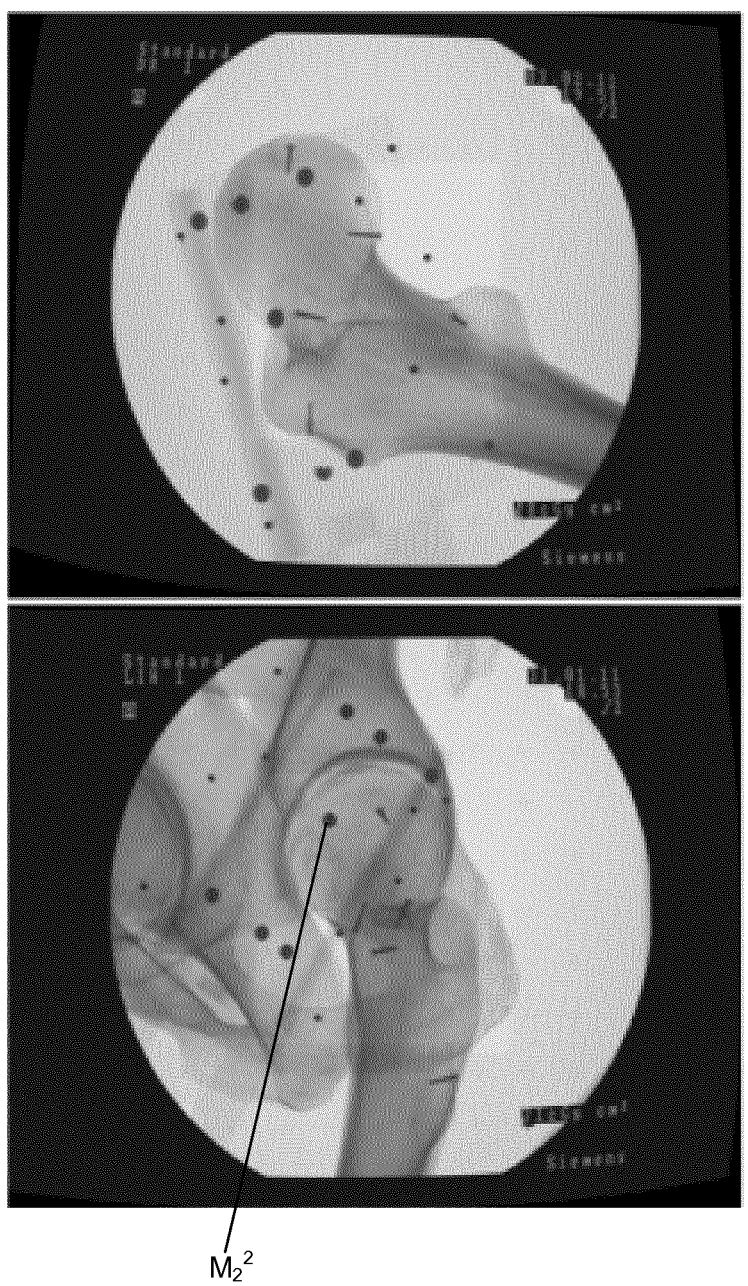
FIG. 8 shows two examples of phantom detection.

Since the distribution of the fiducial projections in the normalized image only depends on the rotation matrices $R^x$ and $R^y$, it is natural to build a look-up table which up to a certain precision (e.g., 1°) contains all the normalized fiducial projections with different combination of $R^x$ and $R^y$. This is done off-line by simulating the projection operation using Eq. (2) based on the pre-calibrated projection model of the x-ray apparatus (C-arm) 3 at the reference position $R_0$, $T_0$ as shown in FIG. 7. For an image acquired at position other than the reference, said normalization operation as described above is automatically applied to all the detected candidate fiducial projections. The normalized candidate fiducial projections are then compared to those in the look-up table to find the best match. Since the items in the look-up table are generated by a simulation procedure, we know exactly the correspondence between the 2D fiducial projections and their corresponding 3D coordinates. Therefore, we can establish the correspondences between the candidate fiducial projections and the fiducials embedded in the phantom. An example of a phantom detection is shown in FIG. 8.

As soon as the correspondences are established, we can further fine-tune the fiducial projection location by applying a cross-correlation based template matching. After that, preferably a direct linear transformation algorithm as described in detail in[13] is used to compute the projection matrix P, i.e. the desired intrinsic and extrinsic parameters.

REFERENCES

1. Yaniv, Z., et al.: Fluroscopic image processing for computer-aided orthopaedic surgery. MICCAI'98, LNCS 1496 (1998) 325-334.
2. Hofstetter, R., et al.: Fluoroscopy as an imaging means for computer assisted surgical navigation. Computer Aided Surgery 4 (1999) 65-76.
3. Livyatan, H., et al.: Robust automatic C-arm calibration for fluoroscopy-based navigation: a practical approach. MICCAI'02, LNCS 2489 (2002) 60-68.
4. Kainz, B., et al.: Fast marker based C-arm pose estimation. MICCAI'08, LNCS 5242 (2008) 652-659.
5. Chintalapani, G., Jain A. K., Taylor, R. H.: Statistical characterization of C-arm distortion with application to intra-operative distortion correction. SPIE Medical Imaging 2007, Vol. 6509 (2007) 65092Y.1-65092Y.8.
6. Chintalapani, G., Taylor, R. H.: C-arm distortion correction using patient CT as fiducial. ISBI 2007, (2007) 1180-1183.
7. Yao, J., et al.: A C-arm fluoroscopy-guided progressive cut refinement strategy using a surgical robot. Computer Aided Surgery 5 (2000) 373-390.
8. Jain, A. and Fichtinger, G.: C-arm tracking and reconstruction without an external tracker. MICCAI'06, LNCS 4190 (2006) 494-502.
9. Otake, Y., et al.: An iterative framework for improving the accuracy of intraoperative intensity-based 2D/3D registration for image-guided orthopedic surgery. IPCAI'10, LNCS 6135 (2010) 23-33.
10. Jollie, I. T.: Principal component analysis (Springer series in statistics). 2nd Edition, 2002, Springer-Verlag, New York.
11. Rajamani, K. T., et al.: Statistical deformable bone models for robust 3D surface extrapolation from sparse data. Medical Image Analysis, 11 (2007) 99-109.
12. OpenCV Library:http://sourceforge.net/projects/opencv-library/files/opencvwin/2.2/
13. Hartley, R. and Zisserman, A.: Multiple view geometry in computer vision. $2^{nd}$ Edition, 2004, Cambridge Univeristy Press.

The invention claimed is:

1. A method for detecting a phantom, comprising the steps of:
    arranging a phantom with respect to an object, the phantom comprising a plurality of first calibration fiducials in a first plane,
    acquiring at least one image of said object by means of an x-ray apparatus, such that the image contains projections of the object as well as projections ($IM_i^1$, $IM_i^2$, $IM_i^3$) of at least three first calibration fiducials,
    detecting the projections of the at least three first calibration fiducials in said at least one image, and
    establishing a correspondence between 2D image coordinates ($I_x$, $I_y$) of said projections of the at least three first calibration fiducials and 3D coordinates (x, y, z) of said at least three first calibration fiducials in a local coordinate system of the phantom for computing a projection matrix (P) at least up to a scale factor ($\alpha$), which projection matrix (P) relates said 2D image coordinates ($I_x$, $I_y$) to said corresponding 3D coordinates (x, y, z) in a local coordinate system of the phantom according to $\alpha[I_x, I_y, 1]^T = P[x,y,z,1]^T$, wherein the at least three first calibration fiducials ($M_i^1$, $M_i^2$, $M_i^3$) corresponding to said detected projections are successively arranged on an associated line of said first plane, wherein the ratio $r_i = |M_i^1 M_i^2|/|M_i^2 M_i^3|$ is different from 1.

2. The method according to claim 1, wherein said correspondence is established using a pinhole camera model for a projection of the x-ray apparatus with a reference position corresponding to extrinsic parameters $R_0$ and $T_0$ according to $$\alpha[I_x, I_y, 1]^T = K(R_0(R^x R^y R^z [x,y,z]^T + T) + T_0),$$

where K is the an intrinsic matrix, $R^x$, $R^y$, $R^z$ are the rotation matrices and T a translation vector from an arbitrary acquisition position to the reference position ($R_0,T_0$), respectively, expressed in the local coordinates of the phantom (x,y,z), wherein from the 3D coordinates of the at least three first calibration fiducials ($M_i^1$, $M_i^2$, $M_i^3$) the intrinsic matrix K, $R_0$ and $T_0$ are determined once for the x-ray apparatus (3) being positioned in the reference position ($R_0$,$T_0$).

3. The method according to claim 1, wherein the projections ($IM_i^1$, $IM_i^2$, $IM_i^3$) of the at least three first calibration fiducials ($M_i^1$, $M_i^2$, $M_i^3$) are transformed and normalized such that the 2D image coordinates ($I_x$, $I_y$) of the projections ($IM_i^1$, $IM_i^2$, $IM_i^3$) of the at least three first calibration fiducials ($M_i^1$, $M_i^2$, $M_i^3$) merely depend on rotations ($R^x$,$R^y$) about an x-axis and a y-axis, wherein said transformation transforms a 2D coordinate system having an origin 0 located at ($IM_i^1$+$IM_i^2$)/2 and an x-axis defined along the direction origin 0→$IM_i^3$ to a coordinate system with its origin at (0, 0) and an x-axis along direction (1, 0), and wherein said transformation normalizes the length of the vector $IM_i^1$→$IM_i^3$ to 1.

4. The method according to claim 3, wherein a lookup table is generated, wherein said lookup table contains all the 2D Image coordinates ($I_x$, $I_y$) of the detected, transformed and normalized projections of the at least three first calibration fiducials for different combinations of rotations ($R^x$,$R^y$) about said x- and y-axis.

5. The method according to claim 4, wherein, for each of the detected, transformed and normalized 2D image coordinates ($I_x$, $I_y$) of the projections of the at least three first calibration fiducials the corresponding 3D coordinates (x, y, z) are taken from the lookup table.

6. The method according to claim 1, wherein projections of at least three further calibration fiducials are detected, wherein at least one of said further calibration fiducials is a second or third calibration fiducial being arranged in a second or third plane of the phantom (20) running parallel to the first plane, wherein the second or third fiducial(s) comprise a smaller volume than the first calibration fiducials.

7. The method according to claim 6, wherein the projection matrix P is computed using the 2D image coordinates ($I_x$, $I_y$) of projections of the at least three first calibration fiducials and the at least three further calibration fiducials as well as the 3D coordinates (x, y, z) of the at least three first calibration fiducials and the 3D coordinates (x, y, z) of the at least three further calibration fiducials.

8. The method, according to claim 1, wherein the method further comprises the following steps, which are performed before acquiring the at least one image of said object:
fixing a fiducial device comprising fiducials with respect to an image detector of an x-ray apparatus, said x-ray apparatus comprising an x-ray generating means-opposing said image detector along a viewing direction of the x-ray apparatus, and wherein the fiducial device comprises a plate carrying said fiducials,
arranging the viewing direction -in different orientations and positions with respect to the earth's magnetic field,
acquiring a model building image ({$I''$}) for each orientation, said model building image containing projections of all fiducials,
detecting positions ({$P_n^i$}) of the projections of the fiducials in the respective model building image ({$I''$}),
computing a displacement vector $D_n$=[$D_{n,x}^1$,$D_{n,y}^1$, . . . , $D_{n,x}^{\tilde{N}_i}$,$D_{n,y}^{\tilde{N}_i}$]$^T$ for each acquired model building image ($I''$), wherein the vectors $D_n^i$=[$D_{n,x}^i$,$D_{n,y}^i$]$^T$ extend from the nominal position ($\bar{P}^i$) of the respective fiducial (i) to the detected position ($P_n^i$) of the projection of said fiducial (i), and wherein
a mean displacement map ($M_D$) as the average of all displacement vectors ($D_n$) is computed and subtracted from each displacement vector ($D_n$) and a principal component analysis is applied to the resulting variation of the displacement vectors ($D_n$) in order to compute eigen displacement maps ({$P_D^i$}) and eigen values ({$\lambda^i$}) of said variation.

9. The method according to claim 8, wherein a part of said plate comprising some of the fiducials is removed from said fiducial device so that, when an image is acquired by means of the x-ray apparatus, the image comprises a corresponding region being free from projections of the fiducials of said part as well as a further region containing projections of remaining boundary fiducials of the fiducial device, which are arranged around said region.

10. The method according to claim 8, wherein at least one image of said object is acquired by means of the x-ray apparatus such that the at least one image contains projections of the object as well as projections of boundary fiducials.

11. The method according to claim 10, wherein the method further comprises the steps of: detecting positions of the projections of the boundary fiducials in the at least one image, computing a corresponding boundary displacement vector $B_n$=[$B_{n,x}^1$,$B_{n,y}^1$, . . . , $B_{n,x}^{\tilde{M}_i}$,$B_{n,y}^{\tilde{M}_i}$]$^T$, wherein the vectors $B_n^i$=[$B_{n,x}^i$,$B_{n,y}^i$]$^T$ extend from the nominal position of the respective boundary fiducial (i) to the detected position of the projection of the respective boundary fiducial (i), and fitting a linear combination $M_D$+$\Sigma_j b_j P_D^i$, where $M_D$ is a mean displacement map and {$P_D^i$} are eigen displacement maps, to the boundary displacement vector ($B_n$) for computing an estimate for the displacement vector ($D_n$) of all fiducials.

12. The method according to claim 11, wherein the method further comprises the step of undistorting the at least one image using the estimated displacement vector ($D_n$) of the at least one image.

13. A Mobile Phantom for an x-ray device, comprising:
a plurality of first calibration fiducials ($M_i^1$, $M_i^2$, $M_i^3$),
a carrier for carrying said first calibration fiducials ($M_i^1$, $M_i^2$, $M_i^3$),
wherein
the phantom comprises three first calibration fiducials ($M_1^1$, $M_1^2$, $M_1^3$) being arranged along a first line, wherein the phantom comprises three further first calibration fiducials ($M_3^1$, $M_3^2$, $M_3^3$) being arranged on a third line running parallel to the first line, and wherein the phantom comprises a further first calibration fiducial ($M_2^2$) arranged on a second line running from a first calibration fiducial ($M_1^2$) that is arranged between two first calibration fiducials ($M_1^1$, $M_1^3$) on the first line to a first calibration fiducial ($M_3^2$) that is arranged between two first calibration fiducials ($M_3^1$, $M_3^3$) on the third line, wherein the second line runs perpendicular to the first and the third line, such that also three first calibration fiducials ($M_2^1$, $M_2^2$, $M_2^3$) are arranged on the second line, wherein the seven first fiducials are all arranged in a first plane, and wherein the three ratios $r_i$=|$M_i^1 M_i^2$|/|$M_i^2 M_i^3$|, i=1, 2, 3, are different from each other.

14. A Fiducial device being designed to be fixed to an image detector of an x-ray apparatus, wherein the fiducial device comprises a plate carrying fiducials, wherein said fiducials are arranged in a single extension plane along which the plate extends, wherein said fiducials are arranged on lattice points of a rectangular lattice, wherein the plate comprises a part containing some of the fiducials, which part is designed to be released from the plate leaving a recess in the plate.

15. The method according to claim 10, wherein said at least one image further contains said projections of the at least three first calibration fiducials.

16. The mobile phantom according to claim 13, wherein the three ratios $r_i = |M_i^1 M_i^2|/|M_i^2 M_i^3|$, $i=1, 2, 3$, are different from 1, and wherein the phantom comprises second calibration fiducials arranged in a second plane running parallel to the first plane, and wherein the phantom comprises third calibration fiducials being arranged in a third plane running parallel to the first and the second plane, wherein the first calibration fiducials ($M_i^1$, $M_i^2$, $M_i^3$) have a larger diameter than the second or third calibration fiducials.

17. A method for building a statistical model for image distortion correction, wherein the method comprises the following steps:

fixing a fiducial device comprising fiducials with respect to an image detector of an x-ray apparatus comprising an x-ray generating means opposing said image detector along a viewing direction of the x-ray apparatus, wherein the fiducial device comprises a plate carrying said fiducials, arranging the viewing direction in different orientations and positions with respect to the earth's magnetic field, acquiring a model building image ($\{I^n\}$) for each orientation, said model building image containing projections of all fiducials, detecting positions ($\{P_n^i\}$) of projections of the fiducials in the respective model building image ($\{I^n\}$), computing a displacement vector $D_n = [D_{n,x}^1, D_{n,y}^1, \ldots, D_{n,x}^{N_i}, D_{n,y}^{N_i}]^T$ for each acquired model building image ($I^n$), wherein the vectors $D_n^i = [D_{n,x}^i, D_{n,y}^i]^T$ extend from the nominal position ($P^i$) of the respective fiducial (i) to the detected position ($P_n^i$) of the projection of said fiducial (i), and wherein a mean displacement map ($M_D$) as the average of all displacement vectors ($D_n$) is computed and subtracted from each displacement vector ($D_n$) and a principal component analysis is applied to the resulting variation of the displacement vectors ($D_n$) in order to compute eigen displacement maps ($\{P_D^i\}$) and eigen values ($\{\lambda^i\}$) of said variation.

* * * * *